(12) United States Patent
Chang et al.

(10) Patent No.: US 9,494,597 B2
(45) Date of Patent: Nov. 15, 2016

(54) HUMAN CONTROL ANTIBODIES AND USES THEREFOR

(71) Applicant: AB BIOSCIENCES, INC., Allston, MA (US)

(72) Inventors: Hsiu-Ching Chang, Lexington, MA (US); Yen-Ming Hsu, Lexington, MA (US); Jeng-Shin Lee, Lincoln, MA (US)

(73) Assignee: AB BIOSCIENCES, INC., Allston, MA (US)

( * ) Notice: Subject to any disclaimer, the term of this patent is extended or adjusted under 35 U.S.C. 154(b) by 0 days.

(21) Appl. No.: 14/384,893

(22) PCT Filed: Apr. 2, 2013

(86) PCT No.: PCT/US2013/034969
§ 371 (c)(1),
(2) Date: Sep. 12, 2014

(87) PCT Pub. No.: WO2013/152011
PCT Pub. Date: Oct. 10, 2013

(65) Prior Publication Data
US 2015/0099862 A1 Apr. 9, 2015

Related U.S. Application Data

(60) Provisional application No. 61/619,104, filed on Apr. 2, 2012.

(51) Int. Cl.
| | | |
|---|---|---|
| *C07K 16/00* | (2006.01) | |
| *C07K 16/22* | (2006.01) | |
| *G01N 33/68* | (2006.01) | |
| *G01N 33/94* | (2006.01) | |
| *C07K 16/24* | (2006.01) | |

(52) U.S. Cl.
CPC ........... *G01N 33/6854* (2013.01); *C07K 16/00* (2013.01); *C07K 16/22* (2013.01); *C07K 16/241* (2013.01); *G01N 33/94* (2013.01); *C07K 2317/40* (2013.01); *C07K 2317/565* (2013.01)

(58) Field of Classification Search
CPC  C07K 16/00; C07K 16/22; C07K 2317/565; C07K 2317/54; C07K 2317/55; C06K 16/241
See application file for complete search history.

(56) References Cited

U.S. PATENT DOCUMENTS

| | | |
|---|---|---|
| 4,595,661 A | 6/1986 | Cragle et al. |
| 4,816,567 A | 3/1989 | Cabilly et al. |
| 4,873,316 A | 10/1989 | Meade et al. |
| 5,225,539 A | 7/1993 | Winter |
| 5,272,071 A | 12/1993 | Chappel |
| 5,565,332 A | 10/1996 | Hoogenboom et al. |
| 5,714,350 A | 2/1998 | Co et al. |
| 5,733,743 A | 3/1998 | Johnson et al. |
| 5,871,907 A | 2/1999 | Winter et al. |
| 6,030,982 A * | 2/2000 | Njoroge et al. .............. 514/290 |
| 6,350,861 B1 | 2/2002 | Co et al. |
| 2003/0108548 A1 | 6/2003 | Bluestone et al. |
| 2003/0219845 A1 | 11/2003 | Ruiz et al. |
| 2008/0025979 A1 | 1/2008 | Honjo et al. |

FOREIGN PATENT DOCUMENTS

| | | |
|---|---|---|
| EP | 0171496 B1 | 5/1993 |
| EP | 0264166 B1 | 8/1996 |
| EP | 0125023 B2 | 3/2002 |
| WO | 8601533 A1 | 3/1986 |
| WO | 8702671 A1 | 5/1987 |
| WO | 9106667 A1 | 5/1991 |
| WO | 9945962 A1 | 9/1999 |
| WO | 00/29584 A1 | 5/2000 |
| WO | WO2009/083246 A1 * | 7/2009 |
| WO | 2010088522 A2 | 8/2010 |

OTHER PUBLICATIONS

Lederman et al in Molecular Immunology 28:1171-1181, 1991.*
Colman P. M., Research in Immunology, 145:33-36, 1994.*
Wu et al., J. Mol. Biol. 294: 151-162, 1999.*
Paul, Fundamental Immunology, (textbook), 1993, pp. 292-295.*
Verhoeyen et al. (1988) "Reshaping Human Antibodies: Grafting an Antilysozyme Activity," Science 239:1534-1536.
Wada et al. (1992) "Codon Usage Tabulated From the GenBank Genetic Sequence Data," Nucleic Acids Res., 20(Suppl):2111-2118.
Winoto et al. (1989) "a Novel, Inducible and T Cell-Specific Enhancer Located at the 3' End of the T Cell Receptor α Locus" EMBO J. 8(3):729-733.
Wood et al. (1985) "The Synthesis and In Vivo Assembly of Functional Antibodies in Yeast," Nature 314:446-449.
International Search Report and Written Opinion, International Application No. PCT/US2010/022592, dated Dec. 23, 2010, 6 pages.
Valjakka et al. (2002) "Crystal Structure of an in Vitro Affinity- and Specificity-Matured Anti-Testosterone Fab in Complex with Testosterone: Improved Affinity Results From Small Structural Changes Within The Variable Domains," J. Biological Chem. 277(46):44021-44027.
McCarthy et al. (2001) "Recombinant Technology: Altering the Fine Specificity of an Anti-Legionella Single Chain Antibody by a Single Amino Acid Insertion," J. Immunol. Meth., 251:137-149.
Webster (1888) "Engineering Antibody Affinity and Specificity," Inter. J. Canc. Supp.3:13-16.

(Continued)

*Primary Examiner* — Phuong Huynh
(74) *Attorney, Agent, or Firm* — John M. Garvey; Sanjukta Ghosh; DLA Piper LLP (US)

(57) ABSTRACT

The present invention provides novel, rationally designed human control antibodies for use in various in vivo and in vitro applications. The antibodies of the present invention have well characterized variable domains that have been designed to minimize or eliminate antigen binding without altering gross antibody structure. Using the antibodies of the present invention in various assays allows researchers to distinguish effects that result from specific antigen-antibody interactions from other, non-specific antibody effects.

16 Claims, 10 Drawing Sheets

(56) References Cited

OTHER PUBLICATIONS

Dabbs, ed. (2002) "Techniques of Immunohistochemistry: Principles, Pitfalls, and Standardization," Diagnostic Immunohistochemistry Churchill Livingstone, Philadelphia, PA pp. 17-19.
International Search Report and Written Opinion, International Application No. PCT/US2011/022998, dated Oct. 27, 2011, 9 pages.
Winkler et al. (2000) "Changing the Antigen Binding Specificity by Single Point Mutations of an Anti-p24 (HIV-1) Antibody," J. Immunol. 165:4505-4514.
Notification Concerning Transmittal of International Preliminary Report on Patentability and Written Opinion, International Application No. PCT/US2013/034969, dated Oct. 16, 2014, 7 pages.
Clark et al. (2006) "Affinity Enhancement of an In Vivo Matured Therapeutic antibody Using Structure-Based Computational Design," Prot. Sci. 15:949-960.
Karpusas et al. (2003) "Crystal Structure of the α1β1 Integrin I Domain in Complex With an Antibody Fab Fragment," J. Mol. Biol. 327:1031-1041.
Kusharyoto et al. (2002) "Mapping of a Hapten-Binding Site: Molecular Modeling and Site-Directed Mutagenesis Study of an Anti-Atrazine Antibody," Prot. Eng. 15(3):233-241.
Lippow et al. (2007) "Computational Design of Antibody-Affinity Improvement Beyond In Vivo Maturation," Nat. Biotechnol. 25(10)1171-1176.
Ruffaï et al. (2000) "Binding of an Antibody Mimetic of the Human Low Density Lipoprotein Receptor to Apolipoprotein E is Governed Through Electrostatic Forces," J. Biol. Chem. 275(10):7109-7116.
Reid et al. (2006) "Structure Activity Relationships of Monocyte Chemoattractant Proteins in Complex with a Blocking Antibody," Prot. Eng. Des. Select. 19(7):317-324.
Supplementary European Search Report in EP Appln. No. 11737760.6, dated Jun. 24, 2013, 9 pages.
Paul, ed. (1993) Fundamental Immunology, 3rd Edition, pp. 292-295 (6 pages).
Rudikoff et al. (1982) "Single amino acid substitution altering antigen-binding specificity," Proc. Natl. Acad. Sci. USA 79(6):1979-1983.
Colman (1994) "Effects of amino acid sequence changes on antibody-antigen interactions," Research in Immunology, 145:33-36.
Bendig (1995) "Humanization of Rodent Monoclonal Antibodies by CDR Grafting," Methods: A Companion to Methods in Enzymology, 8:83-93.
Abraham et al. (1979) In Vivo metabolism of a monoclonal IgG cryoglobulin. Clin. Exp. Immunol. 35:89-95.
Dul et al. (1992) "A conditional secretory mutant in an IgL chain is caused by replacement of tyrosine/phenylalaine 87 with histidine." J. Immunol., 149(6)1927-1933.
Hammond et al. (1995) "Quality control in the secretory pathway." Curr. Opin. in Cell Biol. 7:523-529.
Rosenberg (2006) "Effects of Protein Aggregates: An Immunologic Perspective," AAPS J. 8(3)Art.59:E501-E507.
Sassen et al. (1968) "Immunogenic Potency of Human y-Globulin in Mice." Immunol. 14:247-256.
Sigounas et al. (1994) "Half-Life of Polyreactive Antibodies." J. Clin. Immunol. 14(2):134-140.
Amann et al. (1988) "Tightly Regulated tac Promoter Vectors Useful for the Expression of Unfused and Fused Proteins in *Escherichia Coli*," Gene, 69:301-315.
Armour et al. (2003) "Differential Binding to Human FcγRIIa and FcγRIIb Receptors by Human IgG Wildtype and Mutant Antibodies," Mol. Immunol., 40:585-593.
Baldari et al. (1987) "A Novel Leader Peptide Which Allows Efficient Secretion of a Fragment of Human Interleukin 1β in *Saccharomyces cerevisiae*," EMBO J., 6(1):229-234.

Banerji et al. (1983) "A Lymphocyte-Specific Cellular Enhancer is located Downstream of the Joining Region in Immunoglobulin Heavy Chain Genes," Cell, 33:729-740.
Beidler et al. (1988) "Cloning and High Level Expression of a Chimeric Antibody with Specificity for Human Carcinoembryonic Antigen," J. Immunol., 141(11):4053-4060.
Better et al. (1988) "*Escherichia coli* Secretion of an Active Chimeric Antibody Fragment," Science, 240:1041-1043.
Bird et al. (1988) "Single-Chain Antigen-Binding Proteins," Science, 242:423-426.
Byrne et al. (1989) "Multiplex Gene Regulation: A Two-Tiered Approach to Transgene Regulation in Transgenic Mice," Proc. Natl. Acad. Sci. USA, 86:5473-5477.
Camper et al. (1989) "Postnatal Repression of the α-Fetoprotein Gene is Enhancer Independent," Genes & Develop., 3:537-546.
Capel et al. (1994) "Heterogeneity of Human IgG Fc Receptors," Immunomethods 4:25-34.
Chaiken (1981) "Semisynthetic Peptides and Proteins," in Critical Reviews in Biochemistry and Molecular Biology, 11:255-301.
Chothia et al. (1987) "Canonical Structures for the Hypervariable Regions of Immunoglobulins," J. Mol. Biol., 196:901-917.
Daëron (1997) "Fc Receptor Biology," Annu. Rev. Immunol., 15:203-234.
Edlund et al. (1985) "Cell-Specific Expression of the Rat Insulin Gene: Evidence for Role of Two Distint 5' Flanking Elements," Science, 230:912-916.
Goeddel (1990) "Systems for Heterologous Gene Expression," Methods in Enzymol., 185:3-7.
Gottesman (1990) "Minimizing Proteolysis in *Escherichia Coli*: Genetic Solutions," Methods in Enzymol. 185:119-128.
Gutte et al. (1969) "The Total Synthesis of an Enzyme With Ribonuclease A Activity," in Communications to the Editor, J. Am. Chem. Soc. 91(2):501-502.
Huston et al. (1988) "Protein Engineering of Antibody Binding Sites: Recovery of Specific Activity in an Anti-digoxin Single-Chain Fv analogue Produced in *Escherichia coli*," Proc. Natl. Acad. Sci. USA, 85:5879-5883.
Jones et al. (1986) "Replacing the Complementarity-Determining Regions in a Human Antibody With Those From a Mouse," Nature 321:552-525.
Kaiser et al. (1989), "Peptide and Protein Synthesis by Segment Synthesis-Condensation," Science 243:187-192.
Kanda et al., (2006) "Comparison of Biological Activity Among Nonfucosylated Therapeutic IgG1 Antibodies With Three Different N-Linked Fc Oligosaccharides: the High-Mannose, Hybrid, and Complex Types," Glycobiology, 17(1):104-118.
Kaufman et al. (1987) "Translational Efficiency of Polycistronic mRNAs and their Utilization to Express Heterologous Genes in Mammalian Cells," EMBO J., 6(1)187-193.
Kent (1988) "Chemical Synthesis of Peptides and Proteins," Annu. Rev. Biochem. 57:957-989.
Kessel et al., (1990) "Murine Development Control Genes," Science 249:374-379.
Kjer-Nielsen et al. (2004) "Crystal Structure of the Human T Cell Receptor CD3εγ Heterodimer Complexed to the Therapeutic mAb OKT3," Proc Natl Acad Sci USA 101(20):7675-7680.
Kurjan et al. (1982) "Structure of a Yeast Pheromone Gene (MGα): A Putative α-factor Precursor Contains Four Tandem Copies of Mature α-factor," Cell 30:933-943.
Liu et al. (1987) "Chimeric Mouse-Human IgG1 Antibody That Can Mediate Lysis of Cancer Cells," Proc. Natl. Acad. Sci. USA, 84:3439-3443.
Liu et al. (1987) "Production of a Mouse-Human Chimeric Monoclonal Antibody to CD20 With Potent Fc-Dependent Biologic Activity," J. Immunol., 139(10):3521-3526.
Luckow et al. (1989) "High Level Expression of Nonfused Foreign Genes With Autographa Californica Nuclear Polyhedrosis Virus Expression Vectors," Virology, 170:31-39.
MacCullum et al. (1996) "Antibody-Antigen Interactions: Contact Analysis and Binding Site Topography," J. Mol. Biol., 262:732-745.
Merrifield (1986) "Solid Phase Synthesis," Science, 232:341-347.

(56) References Cited

OTHER PUBLICATIONS

Midtvedt et al. (2003) "Individualized T Cell Monitored Administration of ATG Versus OKT3 in Steroid-Resistant Kidney Graft Rejection" Clin. Transplant., 17: 69-74.
Morrison (1985) "Transfectomas Provide Novel Chimeric Antibodies," Science 229:1202-1207.
Nishimura et al. (1987) "Recombinant Human-Mouse Chimeric Monoclonal Antibody specific for Common Acute Lymphocytic Leukemia Antigen," Cancer Res. 47:999-1005.
Pinkert et al. (1987) "An Albumin Enhancer Located 10 kb Upstream Functions Along With its Promoter to Direct efficient, Liver-Specific Expression in Transgenic Mice," Genes & Dev. 1:268-277-276.
Queen et al. (1983) "Immunoglobulin Gene Transcription is Activated by Downstraem Sequence Elements," Cell 33:741-748.
Queen et al. (1989) "A Humanized Antibody That Binds to the Interleukin 2 Receptor," Proc. Natl. Acad. USA, 86:10029-10033.
Raju (2008) "Terminal Sugars of Fc Glycans Influence Antibody Effector Functions of IgGs," Current Opinion in Immunol., 20:471-478.
Ravetch et al. (1991) "Fc Receptors," Annu. Rev. Immunol., 9:457-492.
Riechmann et al. (1998) "Reshaping Human Antibodies for Therapy," Nature 332:323-327.
Roopenian et al. (2007) "FcRn: The Neonatal Fc Receptor Comes of Age," Nat. Rev. Immunol. 7:715-725.
Schultz et al. (1987) "Expression and Secretion in Yeast of a 400-kDa Envelope Glycoprotein Derived From Epstein-Bar Virus," Gene 54:113-123.
Shaw et al. (1988) "Mouse/Human Chimeric Antibodies to a Tumor-Associated Antigen : Biologic Activity of the four Human IgG Subclasses," J. Natl. Cancer Inst. 80(19):1553-1559.
Smith et al. (1983) "Production of Human Beta Interferon in Insect Cells Infected With a Baculovirus Expression Vector," Mol. & Cell. Biol., 3(12):2156-2165.
Smith et al. (1988) "Single-Step Purification of Polypeptides Expressed in *Escherichia coli* as Fusions With Glutathione S-Transferase," Gene 67:31-40.
Studier et al. (1990) "[6] Use of T7 RNA Polymerase to Direct Expression of Cloned Genes," Methods in Enzymol., 185:60-89.
Sun et al. (1987) "Chimeric Antibody With Human Constant Regions and Mouse Variable Regions Directed Against Carcinoma-Associated Antigen," Proc. Natl. Acad. Sci. USA, 84:214-218.
Talbot et al. (1987) "Catabolism of Homologous Murine Monoclonal Hybridoma IgG Antibodies in Mice," Immuno., 60:485-489.
Thorpe et al. (1982) "The Preparation and Cytotoxic Properties of Antibody-Toxin Conjugates," Immunol. Rev., 62:119-158.

\* cited by examiner

ANTIBODY PRODUCTION OF AVASTIN AND VARIANTS IN 293T TRANSFECTION (ng/ml)

| HEAVY CHAIN / LIGHT CHAIN | | wild type | CDR H1m1 | CDR H2m1 | CDR H2m2 | CDR H3m1 | CDR H13m1 |
|---|---|---|---|---|---|---|---|
| | | NA | N50A/Y51A | N71A/Y73A/Y79A | N71A/Y73A | Y118A/Y121A/Y122A/S124A/S125A | N50A/Y51A/Y118A/Y121A/Y122A/S124A/S125A |
| wild type | NA | 294.9 | 546.4 | 138.5 | 100.1 | 493.4 | 478.9 |

FIG. 3

MUTATIONS WITHIN THE CDRs ABOLISH AVASTIN BINDING TO RECOMBINANT
HUMAN VEGF PROTEIN (OD405)

| HEAVY CHAIN | | wild type | CDR H1m1 | CDR H2m1 | CDR H2m2 | CDR H3m1 | CDR H13m1 |
|---|---|---|---|---|---|---|---|
| | LIGHT CHAIN | NA | N50A/Y51A | N71A/Y73A/Y79A | N71A/Y73A | Y118A/Y121A/Y122A/S124A/S125A | N50A/Y51A/Y118A/Y121A/Y122A/S124A/S125A |
| wild type | NA | WT | V.1 | V.2 | V.3 | V.4 | V.5 |

AVASTIN VARIANTS

FIG. 4

ANTIBODY PRODUCTION OF HUMIRA AND VARIANTS IN 293T TRANSFECTION (ng/ml)

| HEAVY CHAIN | | wild type | CDR H1m1 | CDR H2m1 | CDR H3m1 | CDR H3m2 |
|---|---|---|---|---|---|---|
| LIGHT CHAIN | | NA | N50A/Y51A | S74A/Y79A/S82A | S119A/Y120A/Y129A | L121A/D128A |
| wild type | NA | 1462.4 | 1937.7 | 603.7 | 2732.2 | 1662.1 |
| CDR L1m1 | S48A/Y54A | 896.3 | 945.2 | 196.9 | 453.3 | 728.9 |
| CDR L2m1 | S74A | 1100.5 | 1126.8 | 175.0 | 1467.1 | 1260.0 |
| CDR L3m1 | Y113A/Y118A | 535.4 | 998.8 | 94.5 | 2426.9 | 296.2 |

FIG. 5

MUTATIONS WITHIN THE CDRs ABOLISH HUMIRA BINDING TO RECOMBINANT HUMAN TNFα PROTEIN (OD405)

| HEAVY CHAIN / LIGHT CHAIN | | wild type NA | CDR H1m1 N50A/Y51A | CDR H2m1 S74A/Y79A/S82A | CDR H3m1 S119A/Y120A/Y129A | CDR H3m2 L121A/D128A |
|---|---|---|---|---|---|---|
| wild type | NA | WT | V.1 | V.2 | V.3 | V.4 |
| CDR L1m1 | S48A/Y54A | V.5 | V.6 | V.7 | V.8 | V.9 |
| CDR L2m1 | S74A | V.10 | V.11 | V.12 | V.13 | V.14 |
| CDR L3m1 | Y113A/Y118A | V.15 | V.16 | V.17 | V.18 | V.19 |

HUMIRA VARIANTS

HUMAN CONTROL ANTIBODIES AND USES THEREFOR

CROSS REFERENCE TO RELATED APPLICATIONS

This application is a national phase under 35 U.S.C. §371 of International Patent Application No. PCT/US13/34969, filed Apr. 2, 2013, which claims priority to and the benefit of U.S. Provisional Patent Application No. 61/619,104 entitled "Novel Human Control Antibodies and Uses Therefor," filed Apr. 2, 2012, the contents of each of which are incorporated herein by reference.

REFERENCE TO SEQUENCE LISTING

The instant application contains a Sequence Listing which has been submitted in ASCII format via EFS-Web and is hereby incorporated by reference in its entirety. Said ASCII copy, created on Apr. 5, 2013, is named ABB_004_SL.txt and is 49,386 bytes in size.

BACKGROUND OF THE INVENTION

In order to properly demonstrate the specific binding or biological activities of an antibody, a reference antibody (i.e., a "control") is necessary. Without proper controls, it is difficult to determine the specificity of binding or establish a causal relationship between the specific binding activity and the biochemical and biological effects of an antibody.

In general, two major types of control agents are in use for testing antibodies. The first control is the buffer that is used in the preparation of the testing antibody, such as phosphate buffered saline. The second type of control agent is an antibody that does not share the antigen specificity with the testing antibody. While the antibody control is clearly the better choice, it is far from ideal. This is due to the fact that while most of these antibodies do not recognize the antigen of interest, they retain fully functional complementarity determining regions (CDRs) and are fully capable for interaction with other antigen molecules. Such interactions often produce inexplicable experimental outcomes in the in vitro tests and in studies using animal models. In fact, it is not uncommon that a researcher moves from one control antibody to another until he/she comes across an antibody that gives the least background signals. Clearly, there is a great unmet need for improved, rationally designed control antibodies.

SUMMARY OF THE INVENTION

In one aspect, the present invention provides control antibodies, which are comprised of well-defined variable domains that lack antigen affinity but maintain a native antibody structure. The novel control antibodies allow researchers to distinguish effects that result from specific antigen-antibody interactions as opposed to non-specific antibody effects. Antibodies of the present invention are therefore useful as controls in a wide range of applications that utilize antibody reagents, including flow cytometry, immunoblotting (e.g., dot blotting, western blotting), immunohistochemistry, immunoprecipitation, ELISA, fluorescence microscopy, cellular isolation, cellular purification, protein purification, and other antibody based assays. Antibodies of the invention are also useful as controls in in vitro and in vivo assays in which antibodies are used to elicit a specific cellular response (e.g., cellular proliferation, cellular differentiation, apoptosis, etc.) and for therapeutic applications, both in humans and in non-human animals.

In some embodiments, the antibodies of the invention are comprised of a heavy chain variable region that contains a framework 1 region (FRH1); a first complementary determining region (CDRH1), which is SEQ ID NO: 1 or SEQ ID NO: 2; a framework 2 region (FRH2); a second complementary determining region (CDRH2), which is SEQ ID NO: 3, SEQ ID NO: 4 or SEQ ID NO: 5; a framework 3 region (FRH3); a third complementary determining region (CDRH3), which is SEQ ID NO: 6, or SEQ ID NO: 7 and a framework 4 region (FRH4); wherein the antibody has no specific binding affinity to the human vascular endothelial growth factor (VEGF). In some embodiments FRH1, FRH2, FRH3 or FRH4 is selected from the group consisting of SEQ ID NOs: 11, 12, 13, and 14. In certain embodiments the heavy chain variable region has an amino acid sequence as set forth in any of SEQ ID NOs: 19-30.

In some embodiments, the antibodies of the invention comprises a light chain variable region containing a framework 1 region (FRL1), a first complementary determining region (CDRL1), which is SEQ ID NO: 8, a framework 2 region (FRL2), a second complementary determining region (CDRL2), which is SEQ ID NO: 9, a framework 3 region (FRL3), a third complementary determining region (CDRL3), which is SEQ ID NO: 10 and a framework 4 region (FRL4). In some embodiments FRL1, FRL2, FRL3 or FRL4 is selected from the group consisting of SEQ ID NOs: 15, 16, 17 and 18. In certain embodiments the light chain variable region has an amino acid sequence of SEQ ID NO: 31.

In some embodiments, the antibodies of the invention are comprised of a heavy chain variable region that contains a framework 1 region (FRH1); a first complementary determining region (CDRH1), which is SEQ ID NO: 32 or SEQ ID NO: 33; a framework 2 region (FRH2); a second complementary determining region (CDRH2), which is SEQ ID NO: 34, SEQ ID NO: 35; a framework 3 region (FRH3); a third complementary determining region (CDRH3), which is SEQ ID NO: 36, SEQ ID NO: 37 or SEQ ID NO: 38 and a framework 4 region (FRH4); wherein the antibody has no specific binding affinity to the human tumor necrotic factor (TNF). In some embodiments FRH1, FRH2, FRH3 or FRH4 is selected from the group consisting of SEQ ID NOs: 45, 46, 47 and 48. In certain embodiments the heavy chain variable region has an amino acid sequence as set forth in any of SEQ ID NOs: 53-64.

In some embodiments, the antibodies of the invention comprises a light chain variable region containing a framework 1 region (FRL1), a first complementary determining region (CDRL1), which is SEQ ID NO: 39 or SEQ ID NO: 40, a framework 2 region (FRL2), a second complementary determining region (CDRL2), which is SEQ ID NO: 41 or SEQ ID NO: 42, a framework 3 region (FRL3), a third complementary determining region (CDRL3), which is SEQ ID NO: 43 and SEQ ID NO: 44 and a framework 4 region (FRL4). In some embodiments FRL1, FRL2, FRL3 or FRL4 is selected from the group consisting of SEQ ID NOs: 49, 50, 51 and 52. In certain embodiments the light chain variable region has an amino acid sequence as set forth in SEQ ID NOs: 65-72.

In some embodiments, the antibodies of the invention further comprise a heavy chain constant domain selected from the group consisting of IgM, IgG, IgA, IgD and IgE and/or a light chain constant domain selected from the group consisting of kappa and lambda light chains. In some embodiments the heavy chain is aglycosylated. In certain embodiments the antibody is humanized and/or conjugated to a detectable moiety, a therapeutic agent or a cytotoxic agent.

In some embodiments the antibodies of the invention have a dissociation constant ($K_D$) of greater than or equal to about $10^{-7}$.

In another aspect, the present invention provides an isolated antibody or antibody fragment having a plurality of framework regions comprising the sequences of the Avastin® antibody or fragment, and further having a heavy chain variable region comprising one or more mutations in: a first complementary determining region (CDRH1); or a second complementary determining region (CDRH2); or a third complementary determining region (CDRH3), the CDRH1, CDRH2 or CDRH3 substituting for the corresponding CDRH1, CDRH2 or CDRH3 of an Avastin® reference antibody, the isolated antibody or antibody fragment having reduced specific binding affinity to human VEGF target antigen as compared to the Avastin® reference antibody.

In one embodiment, the isolated antibody or antibody fragment has at least two of the heavy chain complementary determining regions that are mutated. In another embodiment, the CDRH1 region contains a mutation relative to the Avastin® reference antibody. In a further embodiment, the CDRH1 is SEQ ID NO: 2.

In one embodiment, the CDRH2 region contains a mutation relative to the Avastin® reference antibody. In another embodiment, the CDRH2 is SEQ ID NO: 4 or SEQ ID NO: 5. In yet another embodiment, the CDRH3 region contains a mutation relative to the Avastin® reference antibody. In a further embodiment, the CDRH3 is SEQ ID NO: 7. In another embodiment, the CDRH1 and CDRH3 regions are mutated relative to the Avastin® reference antibody. In a further embodiment, the CDRH1 is SEQ ID NO: 2 and the CDRH3 is SEQ ID NO: 7.

In one embodiment, the isolated antibody or antibody fragment exhibits at least 50 fold reduced specific binding affinity to the target antigen as compared to the Avastin® reference antibody. In another embodiment, the isolated antibody or antibody fragment exhibits substantially no detectable specific binding affinity to the target antigen as compared to the Avastin® reference antibody. In a further embodiment, the isolated antibody or antibody fragment having a dissociation constant ($K_D$) of greater than or equal to about $10^{-7}$ relative to the Avastin® reference antibody.

In another aspect, the present invention provides an isolated antibody or antibody fragment having a plurality of framework regions comprising the sequences of the Humira® antibody or fragment, and further having a light chain variable region comprising one or more mutations in: a first complementary determining region (CDRL1); or a second complementary determining region (CDRL2); or a third complementary determining region (CDRL3), the CDRL1, CDRL2 or CDRL3 substituting for the corresponding CDRL1, CDRL2 or CDRL3 of a Humira® reference antibody, the isolated antibody or antibody fragment having reduced specific binding affinity to human TNF target antigen as compared to the Humira® reference antibody.

In one embodiment, the CDRL3 region contains a mutation relative to the Humira® reference antibody. In another embodiment, the CDRL3 is SEQ ID NO: 44.

In one embodiment, CDRL1 region contains a mutation relative to the Humira® reference antibody. In another embodiment, the isolated antibody or antibody fragment has at least two of the light chain complementary determining regions that are mutated. In a further embodiment, the CDRL1 is SEQ ID SEQ ID NO: 44.

In one embodiment, the isolated antibody or antibody fragment further having at least one mutation in a heavy chain complementary determining region CDRH1, CDRH2, or CDRH3.

In another embodiment, the CDRL3 is SEQ ID NO: 44 and the CDRH1 is SEQ ID NO: 33. In yet another embodiment, the CDRL3 is SEQ ID NO: 44 and the CDRH2 is SEQ ID NO: 35. In one embodiment, the CDRL3 is SEQ ID NO: 44 and the CDRH3 is SEQ ID NO: 37. In another embodiment, the CDRL3 is SEQ ID NO: 44 and the CDRH3 is SEQ ID NO: 38. In a further embodiment, the CDRL1 is SEQ ID NO: 40 and the CDRH3 is SEQ ID NO: 38.

In one embodiment, the isolated antibody or antibody fragment exhibits at least 50 fold reduced specific binding affinity to the target antigen as compared to the Humira® reference antibody. In another embodiment, the isolated antibody or antibody fragment exhibits substantially no detectable specific binding affinity to the target antigen as compared to the Humira® reference antibody. In a further embodiment, the isolated antibody or antibody fragment has a dissociation constant ($K_D$) of greater than or equal to about $10^{-7}$ relative to the Humira® reference antibody.

In one embodiment, the isolated antibody or antibody fragment further consists of lambda or kappa light chains.

In another embodiment, the isolated antibody or antibody fragment is conjugated to a detectable moiety, a therapeutic agent, or a cytotoxic agent.

In a further embodiment, the isolated antibody or antibody fragment is selected from the group consisting of: (a) a whole immunoglobulin molecule; (b) an scFv; (c) an Fab fragment; (d) an Fab' fragment; (e) an F(ab')2; (f) an Fv; (g) an Fd fragment; and (h) a disulfide linked Fv.

In one embodiment, the heavy chain variable region of the isolated antibody or antibody fragment relative to the Avastin® reference antibody has an amino acid sequence as set forth in any of SEQ ID NOs: 20-30.

In another embodiment, the heavy chain variable region of the isolated antibody or antibody fragment relative to the Humira® reference antibody has an amino acid sequence as set forth in any of SEQ ID NOs: 54-64. In a further embodiment, the light chain variable region of the isolated antibody or antibody fragment relative to the Humira® reference antibody has an amino acid sequence as set forth in any of SEQ ID NOs: 66-72.

In another embodiment, the isolated antibody further has an Fc domain with altered glycosylation as compared to the Avastin® or Humira® reference antibody.

Based on the teachings of the present invention, those skilled in the art can appreciate that one or more mutations can be introduced into the various heavy or light chain complimentary determining regions, either alone or in combination, (e.g., multiple heavy chain CDR mutations, multiple light chain CDR mutations, both heavy and light chain CDR mutations) to obtain control antibodies or antibody fragments, that having reduced or no detectible specific binding for the targets of their respective reference antibodies.

BRIEF DESCRIPTION OF THE DRAWINGS

FIG. 1 shows an exemplary schematic diagram of an antibody structure, including the CDR regions, variable domains, the Fab domain and the Fc domain.

FIG. 2 shows a schematic representation of an exemplary method of recombinant antibody production.

FIG. 3 shows antibody productivity of stable cell lines expressing Avastin® (wild type heavy chain and wild type light chain) and some exemplary control antibodies of the invention.

FIG. 4 shows ELISA analysis of binding of Avastin® (wild type heavy chain and wild type light chain), and reduced binding of some exemplary control antibodies, to human VEGF.

FIG. 5 shows antibody productivity of stable cell lines expressing Humira® (wild type heavy chain and wild type light chain) and some exemplary control antibodies of the invention.

FIG. 6 shows ELISA analysis of binding of Humira® (wild type heavy chain and wild type light chain), and reduced binding of some exemplary control antibodies, to human TNF.

DETAILED DESCRIPTION OF THE INVENTION

Figure 1:
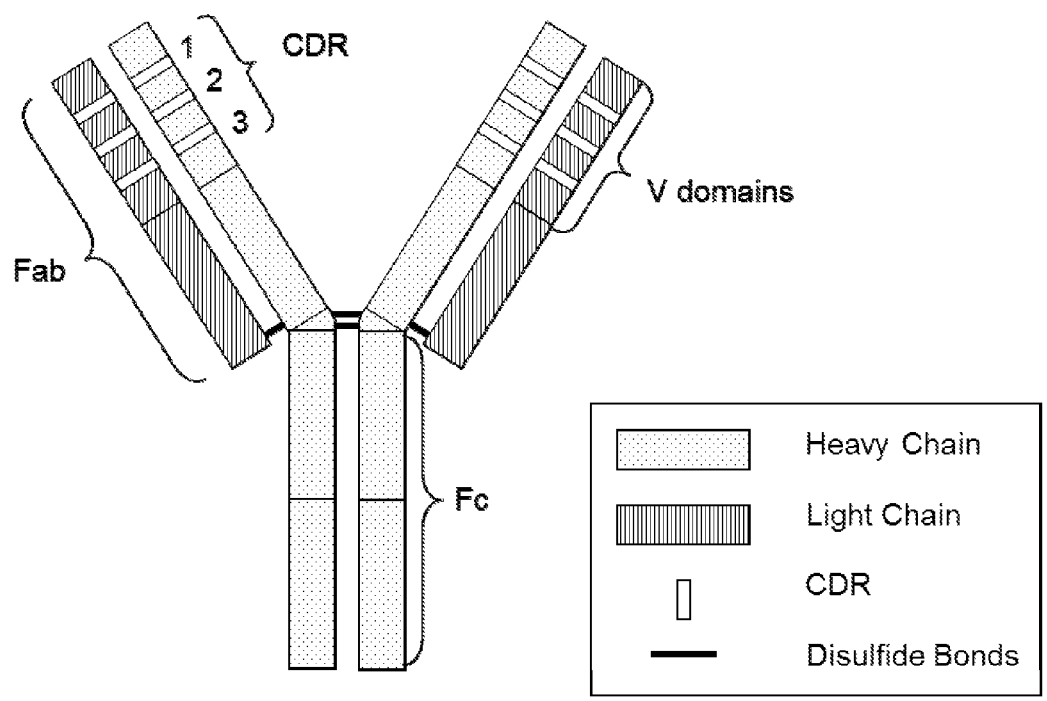
Figure 2:
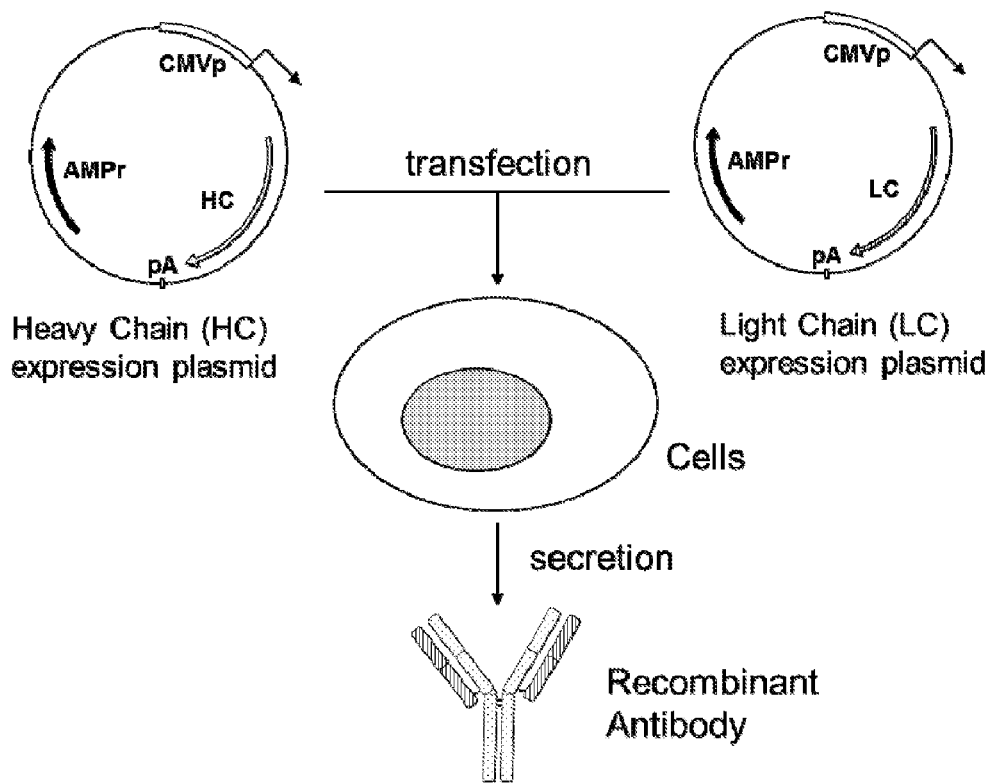

The present invention provides novel, control antibodies, which have well characterized variable domains that minimize or eliminate antigen binding without altering gross antibody structure. In order for the present invention to be more readily understood, certain terms and phrases are defined below as well as throughout the specification.

As used herein, the term "antibody" includes whole antibodies and any antibody fragment, or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region ($V_H$) and a heavy chain constant region. Each light chain is also comprised of a variable region ($V_L$) and a constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Examples of antibody fragments include (i) a Fab fragment, a monovalent fragment consisting of the $V_H$, $V_L$, CL and CH1 domains; (ii) a F(ab')$_2$ fragment, a bivalent fragment comprising two Fab fragments linked by disulfide bridges at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "hypervariable region," "HVR," or "HV," refers to the regions of an antibody-variable domain that are hypervariable in sequence and form structurally defined loops. Generally, antibodies comprise six HVRs; three in the VH (H1, H2, H3), and three in the VL (L1, L2, L3). In an antibody molecule, the three HVRs of a VH domain and the three HVRs of a VL domain are brought together in three-dimensional structure to form an antigen binding surface. Because these sequences form a surface that is complementary to the three dimensional structure of the target antigen, the HVRs are also known as complementarity-determining regions (CDRs). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The end of the Chothia CDR-H1 loop when numbered using the Kabat numbering convention varies between H32 and H34 (see below) depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The residues from each of these hypervariable regions are noted below.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32, 33 or 34 |
| (Kabat Numbering) | | | |
| H1 | H31-H35 | H26-H35 | H26-H32 |
| (Chothia Numbering) | | | |
| H2 | H50-H65 | H50-H58 | H52-H56 |
| H3 | H95-H102 | H95-H102 | H95-H102 |

Hypervariable regions may comprise "extended hypervariable regions" as follows: 24-34 (L1), 50-56 (L2) and 89-97 (L3) in the VL and 26-35B (H1), 50-65 (H2) and 95-102 (H3) in the VH. These extended hypervariable regions are typically combinations of the Kabat and Chothia definitions. The variable domain residues are numbered according to Kabat et al., supra for each of these definitions.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5$^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety).

"Framework region" or "FR" residues are those variable-domain residues other than the HVR residues as herein defined. Exemplary framework regions are provided as SEQ ID NOs. 15-22.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include IgG, IgM, IgA, IgD and IgE.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995). Other FcRs, including those binding to other isotypes as well as those to be identified in the future, are encompassed by the term "FcR" herein.

Antibodies may be polyclonal or monoclonal; xenogeneic, allogeneic, or syngeneic; or modified forms thereof (e.g., humanized, chimeric, etc.). Antibodies may also be fully human. The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising human heavy and light chain transgenes fused to an immortalized cell.

In some embodiments of the invention, antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (see http://www.cbs.dtu.dk/services/NetNGlyc/ for predicting N-linked glycosylation sites) and http://www.cbs.dtu.dk/services/NetOGlyc/ for predicting O-linked glycosylation sites). Additional methods for altering glycosylation sites of antibodies are described in U.S. Pat. Nos. 6,350,861 and 5,714,350.

As used herein, the term an "isolated" refers to a molecule, which is substantially pure.

As used herein, the term "humanized antibody" refers to an antibody that consists of the CDR of antibodies derived from mammals other than human, and the FR region and the constant region of a human antibody. A humanized antibody is useful as an effective component in a therapeutic agent since antigenicity of the humanized antibody in human body is lowered.

As used herein, the term "recombinant antibody" includes all antibodies that are prepared, expressed, created or isolated by recombinant means, such as (a) antibodies isolated from an animal (e.g., a mouse) that is transgenic or transchromosomal for immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such recombinant antibodies have variable and constant regions derived from germline and/or non-germline immunoglobulin sequences. In certain embodiments, however, such recombinant antibodies can be subjected to in vitro mutagenesis (or, when an animal transgenic for Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the germline repertoire in vivo.

As used herein, the term "$K_D$" is intended to refer to the dissociation equilibrium constant of a particular antibody-antigen interaction. In some instances, antibodies can form multivalent interactions with antigen. In such cases, the apparent dissociation equilibrium constant of an antibody/antigen interaction may vary from the monovalent dissociation constant.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined, for example, by surface plasmon resonance (SPR) technology in a BIA-CORE instrument using recombinant proteins as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen". An antibody that has "no specific binding affinity" binds to an antigen with a $K_D$ of approximately greater than $10^{-7}$ M, such as approximately greater than $10^{-6}$ M, $10^{-5}$ M, $10^{-4}$ M, $10^{-3}$ M, $10^{-2}$ M or $10^{-1}$ M, or even greater.

As used herein, the term "isotype" refers to the antibody class (e.g., IgM or IgG) that is encoded by heavy chain constant region genes.

As used herein, the term "nucleic acid molecule" or "polynucleotide" is intended to include DNA molecules and RNA molecules. A nucleic acid molecule may be single-stranded or double-stranded, but preferably is double-stranded DNA.

The present invention also encompasses "conservative sequence modifications" of the sequences set forth in the figures, including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequence set forth in the figures by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Accordingly, antibodies encoded by the heavy and light chain variable region nucleotide sequences disclosed herein and/or containing the heavy and light chain variable region amino acid sequences disclosed herein include substantially similar antibodies encoded by or containing similar sequences which have been conservatively modified. Further discussion as to how such substantially similar antibodies can be generated based on the sequences (i.e., heavy and light chain variable regions) disclosed herein is provided below.

In addition, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, the term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding a ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term "contacts" between an antibody and an antigen refers to interactions between amino acids of an antibody and antigenic determinants of an antigen that contribute to antibody/antigen binding. Such contacts can involve the formation of salt bridges, hydrogen bonds and/or van der Waals force between the antibody and the antigen.

Various aspects of the invention are described in further detail in the following subsections.

I. Control Antibodies

Control antibodies of the present invention are antibodies with well defined variable domains that were rationally designed to eliminate or minimize antigen binding. Control antibodies of the present invention are useful as control reagents in many in vivo and in vitro assays that involve the use of antibodies.

Control antibodies of the invention can be produced using a variety of known techniques, such as the recombinant DNA techniques and other standard molecular and cell biology techniques.

Recombinant control antibodies can be made using recombinant DNA techniques and gene transfection methods well known in the art (Morrison, S. (1985) Science 229: 1202). For example antibody-encoding polynucleotides can be amplified by standard molecular biology techniques (e.g. polymerase chain reaction) and ligated into an expression vector (e.g. pME). Expression vectors encoding the cloned antibody heavy and light chain genes can be transfected into host cells (e.g. 293T cells, CHO-cells) using techniques known in the art (e.g. calcium phosphate precipitation, electroporation, lipofection).

In another embodiment control antibodies can be generated as chimeric antibodies in which the variable regions of the antibody heavy and/or light chains are fused to constant domains from various species.

In addition, humanized control antibodies can be made according to standard protocols such as those disclosed in U.S. Pat. No. 5,565,332. In another embodiment, antibody chains can be produced by recombination between vectors comprising nucleic acid molecules encoding a fusion of a polypeptide chain of a specific antibody chain and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743.

Control antibodies of the invention can be produced using recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In still another aspect of the invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of a specific antibody by constructing expression vectors that include CDR sequences from the specific antibody grafted onto framework sequences from a different antibody with different properties (see, e.g., Riechmann, L. et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The CDR1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining its utility as a control antibody (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention.

The interaction of antibodies and antibody-antigen complexes with cells of the immune system triggers a variety of responses, collectively called effector functions, through a variety of mechanisms, including, for example, by binding to Fc receptors (FcRs) and/or to the C1q component of the complement system. Effector functions may trigger cytokine release, phagocytosis, endocytosis, cytotoxicity (both antibody-dependant cell-mediated cytotoxicity and complement-mediated cytotoxicity), down regulation of cell surface antigens, and/or apoptosis of targeted cells. In certain instances, antibody effector functions may result in undesirable consequences, including, for example, unwanted inflammation and/or elimination of antigen-bearing cells. Therefore, it may be desirable in many instances to modify antibodies in order to reduce alter antibody effector functions. Accordingly, the present invention further relates to control antibodies with altered effector functions.

Interactions of Fc and FcRs have been mapped to several peptide segments within the Fc region. For example, P238 and S239 of the 231-239 (EU numbering) segments have been identified to be involved in FcR binding. In addition, 316-338 and 274-301 segments separately were found to be critical for Fc binding to FcγRI and FcγRIII, respectively. It has been shown that effector functions can be modified by combining critical segments of the Fc region from different antibody subtypes (such as IgG2 and IgG4) in order to generate antibodies that produce the desired effector functions (Armour K L et al., *Mol. Immunol.* 40, 585-593, 2003). Accordingly, the present invention includes control antibodies that contain modifications that result in altered effector functions. For example, antibodies with altered ability to induce complement mediated cytotoxicity can be generated through modification of the 213-238 segment at the N-terminal of the CH2 region and/or the 318-331 segment at the C-terminal of the CH2 region (i.e. K322A and P329A substitutions can be generated in IgG1 antibodies to reduce binding of the antibodies to C1a and thereby reducing complement mediated cytotoxicity). In another example, control antibodies of the present invention can includes modifications of one or more of these critical amino acid residues for binding to one type of FcR while retaining the ability to bind one or more other types of FcR and/or C1q.

Glycosylation of the canonical Asn297 residue (N-X-S/T signature triplet peptide) at the CH2 of the Fc region also contributes to antibody binding of FcRs and C1q. Removal of this N-glycan reduces antibody bindings to Fc receptors and the C1q complement. Hence, altering glycosylation at Asn297 at the CH2 region of the antibody is another approach to modulate the effector functions of an antibody (Raju, T S, *Current Opinion in Immunol.* 20, 471-478, 2008). In addition, the heterogeneity of Asn297-linked glycans can affect antibody binding to FcRs and C1q. Importantly, loss of the canonical glycans compromises antibody binding to FcRs, but does not affect antibody half life (reviewed in Roopenian D C and Akilesh S. *Nat. Rev. Immunol.* 9, 715-725, 2007). Effector function modification through removal of glycans can be used in combination with the mutated FcR and/or C1q binding sites described above.

In contrast to the reduced effector functions in antibodies with reduced levels of canonical glycans, antibodies with reduced levels of fucose in their sugar chains have enhanced binding to FcγRIIIa. As FcγRIIIa is an important Fc receptor for antibody dependant cell mediated cytotoxicity, low-fucose antibodies exhibit higher ADCC response compared to the conventionally high-fucose antibodies (Kanda S et al, *Glycobiology,* 17, 104-118, 2007).

Thus, the present invention includes control antibodies carrying altered glycosylation. The alteration of N-glycans in the CH2 domain of the heavy chain Fc region may be accomplished by any technique known in the art, including, for example, by mutation of the canonical Asn residue at 297 position, mutation of the canonical Ser or Thr residue at 299 position (to eliminate the tri-peptide N-glycosylation motif, N-X-S/T), enzymatic removal of the glycans (use of PNGase F (peptide N-glycohydrolase)), metabolic blockade of in situ glycosylation (such as use of ER glycosylation inhibitor, tunicamycin, in culture of antibody producing cells), or production of afucosylated antibodies in host cell lines that are deficient in fucosyl transferase (Kanda S et al, *Glycobiology,* 17, 104-118, 2007).

II. Isolated Nucleic Acid Molecules

One aspect of the invention pertains to isolated nucleic acid molecules that encode polypeptides of the present invention as well as nucleic acid fragments sufficient for use as hybridization probes to identify nucleic acid molecules encoding these polypeptides and fragments for use as PCR primers for the amplification or mutation of the nucleic acid molecules. As used herein, the term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention can be isolated using standard molecular biology techniques and the sequence information provided herein. For example, a nucleic acid molecule of the invention can be isolated by the polymerase chain reaction (PCR) using synthetic oligonucleotide primers designed based upon the sequences of the invention.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the invention can be prepared by standard synthetic techniques, e.g., using an automated DNA synthesizer.

In another embodiment, an isolated nucleic acid molecule of the invention comprises a nucleic acid molecule which is a complement to a described nucleic acid molecule. A nucleic acid molecule which is complementary to a described nucleic acid molecule, is one which is sufficiently complementary to a described nucleotide sequence, such that it can hybridize to the respective nucleotide sequence of the invention, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence of the invention, or a portion of any of these nucleotide sequences.

The invention further encompasses nucleic acid molecules that differ from nucleotide sequence(s) that encode polypeptides of the invention due to degeneracy of the genetic code and thus encode the same polypeptides as those encoded by the respective nucleotide sequence. In another embodiment, an isolated nucleic acid molecule of the invention has a nucleotide sequence encoding a polypeptide of the present invention.

Nucleic acid molecules corresponding to homologues of a nucleic acid molecule of the present invention can be isolated based on their homology to the nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising a nucleic acid molecule of the present invention.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further non-limiting example of stringent hybridization conditions includes hybridization at 6×SSC at 45° C., followed by one or more washes in 0.2×SSC, 0.1% SDS at 65° C. A non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6(log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) Proc. Natl. Acad. Sci. USA 81:1991-1995 (or alternatively 0.2×SSC, 1% SDS).

The skilled artisan will further appreciate that changes can be introduced by mutation into a nucleic acid molecule of the present invention, thereby leading to changes in the amino acid sequence of the encoded polypeptides of the present invention, without altering the functional ability of the polypeptides. For example, nucleotide substitutions leading to amino acid substitutions at "non-essential" amino acid residues can be made in a nucleic acid molecule of the present invention. A "non-essential" amino acid residue is a residue that can be altered from a nucleic acid molecule of the present invention without altering the biological property, whereas an "essential" amino acid residue is required for the biological property. For example, amino acid residues that are important for the structural integrity of the antibody molecules, are predicted to be particularly unamenable to alteration.

Accordingly, another aspect of the invention pertains to nucleic acid molecules encoding polypeptides of the present invention that contain changes in amino acid residues that are not essential for activity. Such polypeptides differ in amino acid sequence from those in FIGS. 2-7, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to polypeptides of the invention.

An isolated nucleic acid molecule encoding a polypeptide identical to the polypeptides of the invention can be created by introducing one or more nucleotide substitutions, additions or deletions into the nucleotide sequences of the invention such that one or more amino acid substitutions, additions or deletions are introduced into the encoded polypeptide. Mutations can be introduced into nucleic acid molecules of the present invention by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the invention (e.g., those in FIGS. 2-7) can be replaced with another amino acid residue from the same side chain family. Alternatively, in another embodiment, mutations can be introduced randomly along all or part of a nucleic acid molecule(s) of the present invention, such as by saturation mutagenesis, and the resultant mutants can be screened for biological activity to identify mutants that retain activity. Following mutagenesis of a nucleic acid molecule of the present invention, the encoded polypeptide can be expressed recombinantly and the activity of the polypeptide can be determined.

The expression characteristics of a nucleic acid molecules of the present invention within a cell line or microorganism may be modified by inserting a heterologous DNA regulatory element into the genome of a stable cell line or cloned microorganism such that the inserted regulatory element is operatively linked with the a nucleic acid molecules of the present invention. For example, a heterologous regulatory element may be inserted into a stable cell line or cloned microorganism, such that it is operatively linked with a nucleic acid molecules of the present invention, using techniques, such as targeted homologous recombination, which are well known to those of skill in the art, and described, e.g., in Chappel, U.S. Pat. No. 5,272,071; PCT publication No. WO 91/06667, published May 16, 1991.

III. Isolated Polypeptide Molecules

One aspect of the invention pertains to isolated polypeptides of the present invention (e.g., those that encode the control antibodies of the present invention). In one embodiment, polypeptides of the present invention can be isolated from cells or tissue sources by an appropriate purification scheme using standard protein purification techniques. In another embodiment, polypeptides of the present invention are produced by recombinant DNA techniques. Alternatively, polypeptides of the present invention can be chemically synthesized using standard peptide synthesis techniques.

An "isolated" or "purified" polypeptide is substantially free of cellular material or other contaminating proteins from the cell or tissue source from which the polypeptides of the present invention is derived, or substantially free from chemical precursors or other chemicals when chemically synthesized. The language "substantially free of cellular material" includes preparations of polypeptide(s) of the present invention in which the polypeptide is separated from cellular components of the cells from which it is isolated or recombinantly produced. In one embodiment, the language "substantially free of cellular material" includes preparations of polypeptide(s) of the present invention having less than about 30% (by dry weight) of proteins not of the present invention (also referred to herein as a "contaminating protein"), more preferably less than about 20% of proteins not of the present invention, still more preferably less than about 10% of proteins not of the present invention, and most preferably less than about 5% of proteins not of the present invention. When polypeptides of the present invention are recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of polypeptide(s) of the present invention in which the polypeptide is separated from chemical precursors or other chemicals which are involved in the synthesis of the polypeptide. In one embodiment, the language "substantially free of chemical precursors or other chemicals" includes preparations of polypeptide(s) of the present invention having less than about 30% (by dry weight) of chemical precursors or of proteins not of the present invention, more preferably less than about 20% chemical precursors or of proteins not of the present invention, still more preferably less than about 10% chemical precursors or of proteins not of the present invention, and most preferably less than about 5% chemical precursors or of proteins not of the present invention.

In another embodiment, polypeptide(s) of the present invention (e.g., those that encode the control antibodies of the present invention) has an amino acid sequence that includes one or more of SEQ ID NO: 1-14.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The amino acid sequences of the described polypeptide(s) will enable those of skill in the art to produce corresponding polypeptides. Such polypeptides can be produced in prokaryotic or eukaryotic host cells by expression of polynucleotides encoding a polypeptide(s) of the present invention. Alternatively, such polypeptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference).

IV. Recombinant Expression Vectors and Host Cells

Another aspect of the invention pertains to vectors, preferably expression vectors, containing a nucleic acid molecule encoding a polypeptide of the present invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of polypeptides of the present invention in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in E. coli with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion E. coli expression vectors include pTrc (Amann et al. (1988) Gene 69:301-315) and pET 1 Id (Studier et al. (1990) Methods Enzymol. 185:60-89). Target gene expression from the pTrc vector relies on host RNA polymerase transcription from a hybrid trp-lac fusion promoter. Target gene expression from the pET 11 d vector relies on transcription from a T7 gn 10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in E. coli is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., FIGS. 2-7) can be expressed in insect cells using baculovirus expression vectors. Baculovirus vectors available for expression of polypeptides in cultured insect cells (e.g., Sf 9 cells) include the pAc 'series (Smith et al. (1983) Mol. Cell Biol. 3:2156-2165) and the pVL series (Lucklow and Summers (1989) Virology 170:31-39).

In yet another embodiment, a nucleic acid of the present invention (e.g., FIGS. 2-7) is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

Another aspect of the invention pertains to host cells into which a nucleic acid molecule of the present invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as the polynucleotide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the present invention. Accordingly, the invention further provides methods for producing a polypeptide of the present invention using the host cells of the present invention. In one embodiment, the method comprises culturing the host cell of the invention (into which a recombinant expression vector encoding a polypeptide of the present invention has been introduced) in a suitable medium such that a polypeptide of the present invention is produced. In another embodiment, the method further comprises isolating a polypeptide of the present invention from the medium or the host cell.

The host cells of the invention can also be used to produce non-human transgenic animals, as described below.

V. Antibody Conjugates/Immunotoxins

In another aspect, the present invention features control antibodies conjugated to a therapeutic moiety, such as a cytotoxin, a drug (e.g., an immunosuppressant) or a radioisotope, which can be used as controls in pre-clinical and/or clinical studies designed to examine the safety and efficacy of specific antibodies conjugated similarly for various therapeutic applications. Specific antibodies conjugated to a cytotoxin are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Specific antibodies can also be conjugated to a radioisotope, e.g., radioactive iodine, to generate cytotoxic radiopharmaceuticals for treating a related disorder, such as a cancer.

Conjugated control antibodies can be used as controls in assays designated to diagnostically or prognostically monitor polypeptide levels in tissue as part of a clinical testing procedure, e.g., to, for example, determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The antibody conjugates of the invention can be used as a control in procedures designed to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors. Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

Example 1

Generation and Characterization of Novel Control Antibodies (I)

The amino acid sequences of Avastin® complementarity determining regions were modified to reduce or eliminate antigen binding without affecting antibody structure or expression. Exemplary heavy chain CDR sequences of control antibodies of the invention are listed in Table 1. The resulting control antibodies had the framework regions of the Avastin® antibody, but the modifications to various CDRs produced Avastin® control antibodies that display minimal or no capacity to bind specifically to human VEGF, Avastin®'s target antigen (FIG. 4).

TABLE 1

Exemplary control antibody heavy chain CDR sequences (I).

| CDR | Substitution | Sequence | SEQ ID NO. |
|---|---|---|---|
| Avastin® CDRH1 | NA | GYTFTNYGMN | SEQ ID NO: 1 |
| Avastin® CDRH1m | N50A, Y51A | GYTFTAAGMN | SEQ ID NO: 2 |
| Avastin® CDRH2 | NA | WINTYTGEPT YAADFKR | SEQ ID NO: 3 |
| Avastin® CDRH2m1 | N71A, Y73A, Y79A | WIATATGEPT AAADFKR | SEQ ID NO: 4 |
| Avastin® CDRH2m2 | N71A, Y73A | WIATATGEPT YAADFKR | SEQ ID NO: 5 |
| Avastin® CDRH3 | NA | YPHYYGSSHW YFDV | SEQ ID NO: 6 |
| Avastin® CDRH3m | Y118A, Y121A, Y122A, S124A, S125A | APHAAGAAHW YFDV | SEQ ID NO: 7 |

Example 2

Generation and Characterization of Novel Control Antibodies (II)

The amino acid sequences of Humira® complementarity determining regions were modified to reduce or eliminate antigen binding without affecting antibody structure or expression. Exemplary heavy chain CDR sequences of control antibodies of the invention are listed in Table 2. The resulting control antibodies had the framework regions of the Humira® antibody but modifications to various CDRs produced Humira® control antibodies that display minimal or no capacity to bind specifically to human TNF, Humira®'s target antigen (FIG. 6).

TABLE 2

Exemplary control antibody heavy chain CDR sequences (II).

| CDR | Substitution | Sequence | SEQ ID NO. |
|---|---|---|---|
| Humira® CDRH1 | NA | GFTFDDYAMH | SEQ ID NO: 32 |
| Humira® CDRH1m | D50A, Y51A | GFTFDAAAMH | SEQ ID NO: 33 |
| Humira® CDRH2 | NA | AITWNSGHID YADSVEG | SEQ ID NO: 34 |
| Humira® CDRH2m | S74A, Y79A, S82A | AITWNAGHID AADAVEG | SEQ ID NO: 35 |
| Humira® CDRH3 | NA | VSYLSTASSL DY | SEQ ID NO: 36 |
| Humira® CDRH3m1 | S119A, Y120A, Y19A | VAALSTASSL DA | SEQ ID NO: 37 |
| Humira® CDRH3m2 | L121A, D128A | VSYASTASSL AY | SEQ ID NO: 38 |

Cell Lines and Media

Human 293T cells were maintained in Dulbecco's Modified Eagles's medium (DMEM) supplemented with 10% fetal bovine serum (FBS) (Invitrogen, Gibco, Carlsbad, Calif.), 2 mM L-glutamine, and 40 ug/ml of gentamicin. All media and supplements were purchased from Lonza, Walkville, Md., except for FBS.

Construction of Avastin® and Humira® Heavy and Light Chain Expression Plasmids

The constant regions of human IgG1 heavy chain, and kappa light chain, were cloned by polymerase chain reaction (PCR) using Invitrogen Platinum Taq DNA polymerase High Fidelity (Invitrogen, Cat #11304-029) and human normal spleen PCR ready first strand cDNA (BioChain Institute, Inc., Cat #C1234246) as the template. The amplified fragments were inserted by standard cloning techniques to a mammalian expression plasmid, containing a human cytomegalovirus (CMV) immediate early gene promoter driven cassette. The resultant plasmids, pME-IgHCR-hG1 and pME-IgLCR-k, contain engineered cloning sites for the insertion of variable regions. The coding sequences for the variable regions of Avastin® heavy chain (Accession No. HC869889), Avastin® light chain (Accession No. HC869896), Humira® heavy chain (Accession No. CS480796) and Humira® light chain (Accession No. CS480795), as well as appropriate signal peptides, were synthesized through custom orders by GeneArt (now part of Life Technologies Corporation), and were inserted into pME-IgHCR-hG1 and pME-IgLCR-k. All plasmids were confirmed by sequencing reactions.

Figure 7:
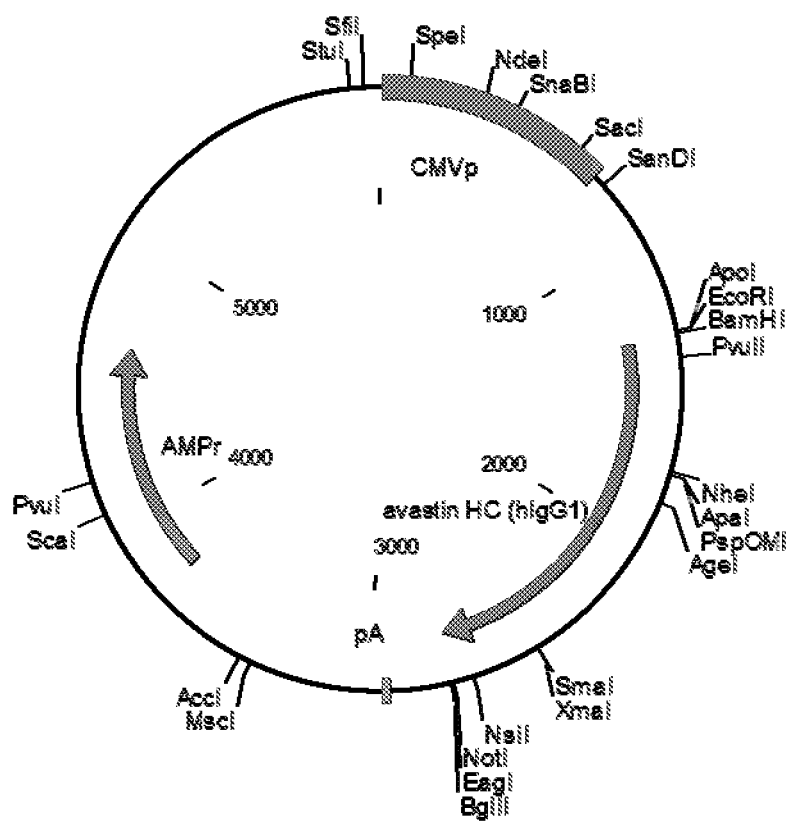
FIG. 7 shows a map of the pME-wt Avastin® HC vector that encodes the Avastin® heavy chain.
Figure 8:
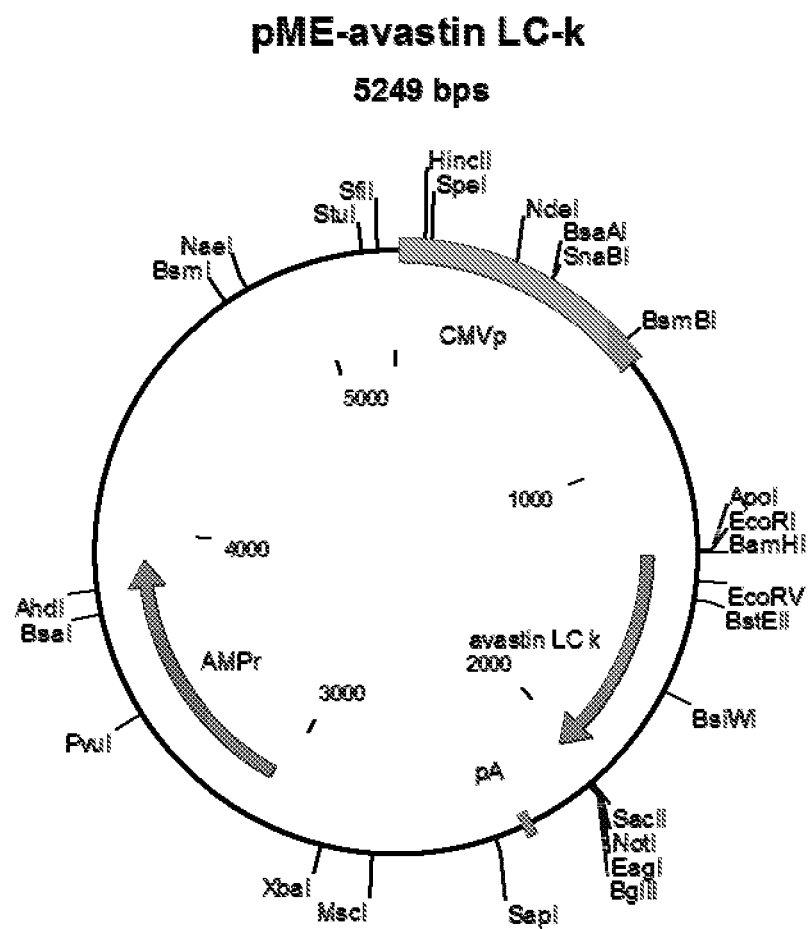
FIG. 8 shows a map of the pME-wt Avastin® LC vector that encodes the Avastin® light chain.
Figure 9:
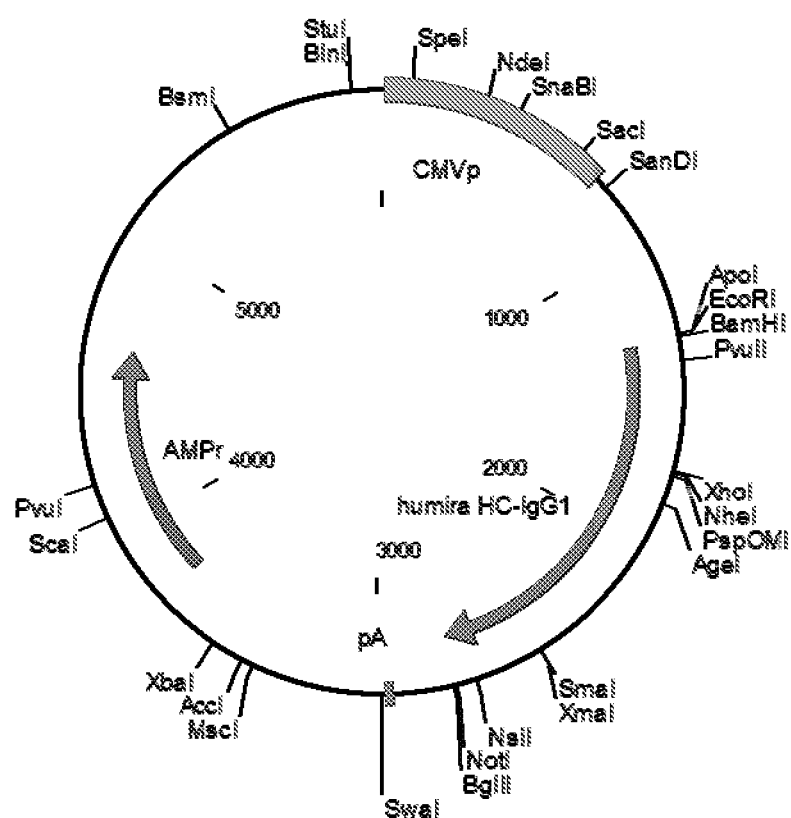
FIG. 9 shows a map of the pME-wt Humira® HC vector that encodes the Humira® heavy chain.
Figure 10:
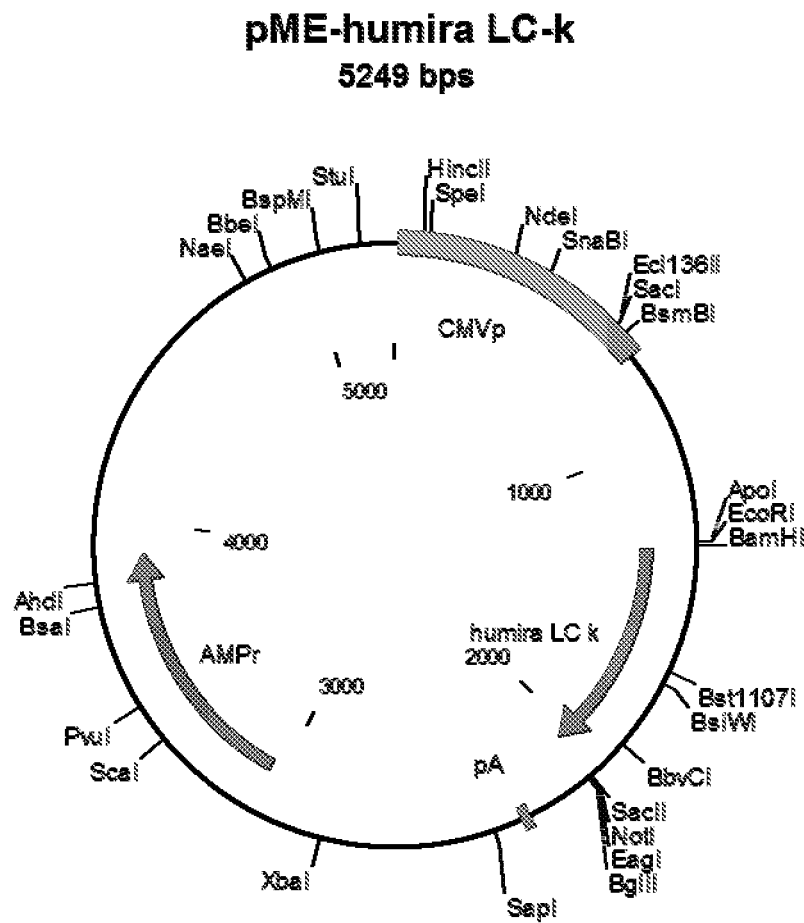
FIG. 10 shows a map of the pME-wt Humira® LC vector that encodes the Humira® light chain.

The engineering of the expression plasmids for the heavy chain and light chain of Avastin®, pME-Avastin® HC-IgG1 and pME-Avastin® LC-k are described in FIG. 7 and FIG. 8, respectively. The engineering of the expression plasmids for the heavy chain or light chain of Humira®, pME-Humira® HC-IgG1 and pME-Humira® LC-k is described in FIG. 9 and FIG. 10, respectively.

Construction of Expression Plasmids Encoding Avastin® and Humira® Heavy and Light Chain Variants Site directed mutagenesis was performed using standard PCR techniques to generate the Avastin® and Humira® heavy and light chain variants, replacing various antigen contacting amino acids within the CDRs with alanine. PCR fragments harboring the mutations were cloned into the same expression plasmids pME-IgHCR-hG1 and pME-IgLCR-k. The mutagenesis was confirmed by sequencing of the resultant plasmids.

Transfection

The Avastin® and Humira® variant antibodies were produced by transient transfection using TransIT-293 Transfection Reagent (Minis Bio LLC). Briefly, human 293T cells were seeded in 6 cm plates at 3×10$^6$ cells/4 ml 293T medium (DMEM+10% heat-inactivated fetal calf serum+6 mM L-Glutamine+40 ug/ml Gentamicin)/plate ~24 hours before transfection. The transfection procedure was carried out by first mixing 4 μg each of the Avastin® or Humira® heavy and light chain plasmid DNAs with 100 μl serum free DMEM. In a separate tube, 24 μl of TransIT-293 Transfection Reagent was added to 100 μl serum free DMEM. The content of both tubes were combined and incubated at room temperature for 10 minutes. The media of the 293T cultures plated the day before were removed, and replaced with 2 ml fresh 293T medium for each 6 cm plate. The DNA/TransIT-293 Transfection Reagent mixture was then slowly added to the cells. 12-16 hours after transfection, the culture medium was changed once again with 4 ml fresh 293T medium per plate. 40-48 hours after transfection, culture supernatants containing Avastin® and Humira® variant antibodies were harvested, and used for subsequent analyses.

Antibody Quantitation

The amount of Avastin® and Humira® variant antibodies produced by transient transfection was determined by the following Sandwich ELISA assay. Briefly, 96-well ELISA microplates (Greiner Bio-one) were pre-coated with 0.1 μg goat anti-human IgG (Jackson ImmunoResearch Laboratories, Inc.) per well overnight at 4° C., followed by blocking with TBS containing 1% bovine serum albumin for 1 hour. Serial dilutions of the transfection supernatants in blocking solution were added to the plates and incubated for 1 hour at room temperature. Washings between the different steps were done with TBS containing 0.05% Tween 20. Bound Avastin® and Humira® variant antibodies were detected by incubation with horseradish peroxidase-conjugated goat anti-human IgG (Jackson ImmunoResearch Laboratories, Inc.) at room temperature for 1 hour. After washings, activity of horseradish peroxidase was measured by a colorimetric method using ABTS 1-Component Microwell Peroxidase Substrate Kit (KPL, Inc.). Color was allowed to develop for 10-30 minutes at room temperature, and absorbance at 405 nm was measured with Molecular Devices SpectraMax 250 Microplate Reader.

Analyses of Specific Antigen-Binding Activities of the Avastin® and Humira® Variant Antibodies The loss of antigen-binding activities of the Avastin® and Humira® variant antibodies were ananlyzed by a similar Sandwich ELISA assay as the one described above. The ELISA microplates were pre-coated with the target antigen proteins, recombinant human VEGF (R&D Systems, Inc.) for the Avastin® series, and recombinant human TNFα (AB Biosciences, Inc.) for the Humira® series. After blocking, transfection supernanants containing the Avastin® and Humira® variant antibodies were added to the plates and incubated for 1 hour at room temperature. Bound Avastin® and Humira® variant antibodies were detected by the same method as described above.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated antibody or antigen binding fragment thereof, comprising: an adalimumab reference antibody having a modification within a CDRL3 region that eliminates TNF-binding, wherein the CDRL3 is SEQ ID NO: 44.

2. An isolated antibody or antigen binding fragment comprising: an adalimumab reference antibody having a modification within a CDRL2 region that eliminates TNF-binding, wherein the CDRL2 is SEQ ID NO: 42.

3. An isolated antibody or antigen binding fragment thereof, comprising: an adalimumab reference antibody having a modification within a CDRL1 region that eliminates TNF-binding, wherein the CDRL1 is SEQ ID NO: 40.

4. The isolated antibody or antigen binding fragment of claim 1, further comprising a modification within a CDRH1 region, wherein the CDRH1 is SEQ ID NO: 33.

5. The isolated antibody or antigen binding fragment of claim 1, further comprising a modification within a CDRH2 region, wherein the CDRH2 is SEQ ID NO: 35.

6. The isolated antibody or antigen binding fragment of claim 1, further comprising a modification within a CDRH3 region, wherein the CDRH3 is SEQ ID NO: 37.

7. The isolated antibody or antigen binding fragment of claim 1, further comprising a modification within a CDRH3 region, wherein the CDRH3 is SEQ ID NO: 38.

8. The isolated antibody or antigen binding fragment of claim 3, further comprising a modification within a CDRH3 region, wherein the CDRH3 is SEQ ID NO: 38.

9. An isolated antibody or antigen binding fragment thereof, comprising: an adalimumab reference antibody having a modification that eliminates TNF-binding, the modification within a heavy chain variable region, wherein the heavy chain variable region has an amino acid sequence selected from the group consisting of SEQ ID NOs: 54-64.

10. An isolated antibody or antigen binding fragment thereof, comprising: an adalimumab reference antibody having a modification that eliminates TNF-binding, the modification within a light chain variable region, wherein the light chain variable region has an amino acid sequence selected from the group consisting of SEQ ID NOs: 66-72.

11. An isolated antibody or antigen binding fragment thereof comprising: an adalimumab reference antibody having modifications that eliminate TNF-binding, wherein the modifications comprise: a light chain CDR1 region having amino acid substitutions S48A and Y54A and a heavy chain CDR3 region having amino acid substitutions L121A and D128A.

12. An isolated antibody or antigen binding fragment, comprising: an adalimumab reference antibody having a modification in a light chain CDR3 region, the modification comprising substitutions Y113A and Y118A relative to the reference antibody.

13. The isolated antibody or antigen binding fragment of claim 12, further comprising a mutation in heavy chain CDR1 region, wherein the mutation comprises amino acid substitutions N50A and Y51A relative to the reference antibody.

14. The isolated antibody or antigen binding fragment of claim 12, further comprising a mutation in heavy chain CDR2 region, wherein the mutation comprises amino acid substitutions S74A, Y79A and S82A relative to the reference antibody.

15. The isolated antibody or antigen binding fragment of claim 12, further comprising a mutation in heavy chain CDR3 region, wherein the mutation comprises amino acid substitutions S119A, Y120A and Y129A relative to the reference antibody.

16. The isolated antibody or antigen binding fragment of claim 12, further comprising a heavy chain CDR3 region, wherein the mutation comprises amino acid substitutions L122A and D128A relative to the reference antibody.

* * * * *

SEQUENCE LISTING

<160> NUMBER OF SEQ ID NOS: 72

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Asn Tyr Gly Met Asn
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Ala Ala Gly Met Asn
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ile Asn Thr Tyr Thr Gly Glu Pro Thr Tyr Ala Ala Asp Phe Lys
1               5                   10                  15

Arg

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ile Ala Thr Ala Thr Gly Glu Pro Thr Ala Ala Ala Asp Phe Lys
1               5                   10                  15

Arg

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Ala Thr Ala Thr Gly Glu Pro Thr Tyr Ala Ala Asp Phe Lys
1               5                   10                  15

Arg

```
<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Pro His Tyr Tyr Gly Ser Ser His Trp Tyr Phe Asp Val
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Pro His Ala Ala Gly Ala Ala His Trp Tyr Phe Asp Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ala Ser Gln Asp Ile Ser Asn Tyr Leu Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Thr Ser Ser Leu His Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Ser Thr Val Pro Trp Thr
1               5

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Val Arg Gln Ala Pro Gly Lys Gly Leu Glu Trp Val Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Phe Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Gly Gln Gly Thr Leu Val Thr Val Ser Ser
1               5                   10

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Trp Tyr Gln Gln Lys Pro Gly Lys Ala Pro Lys Val Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Gly Gln Gly Thr Lys Val Glu Ile Lys Arg
1               5                   10

<210> SEQ ID NO 19
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Ala Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30
```

```
Gly Met Asn Trp Val Arg Gln Ala Pro Gly Lys Gly Leu Glu Trp Val
            35                  40                  45

Gly Trp Ile Ala Thr Ala Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser
            115                 120

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
                100                 105                 110

Trp Gly Gln Gly Thr Leu Val Thr Val Ser Ser
            115                 120

<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
                20                  25                  30

Gly Met Asn Trp Val Arg Gln Ala Pro Gly Lys Gly Leu Glu Trp Val
            35                  40                  45

Gly Trp Ile Ala Thr Ala Thr Gly Glu Pro Thr Ala Ala Ala Asp Phe
    50                  55                  60

Lys Arg Arg Phe Thr Phe Ser Leu Asp Thr Ser Lys Ser Thr Ala Tyr
65                  70                  75                  80
```

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
            100                 105                 110

Trp Gly Gln Gly Thr Leu Val Thr Val Ser Ser
        115                 120

```
<210> SEQ ID NO 27
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Ala Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
            100                 105                 110

Trp Gly Gln Gly Thr Leu Val Thr Val Ser Ser
        115                 120

<210> SEQ ID NO 28
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
            100                 105                 110

Trp Gly Gln Gly Thr Leu Val Thr Val Ser Ser
        115                 120

<210> SEQ ID NO 29
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Ala Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
            100                 105                 110

Trp Gly Gln Gly Thr Leu Val Thr Val Ser Ser
        115                 120

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Ala
            20                  25                  30

Gly Met Asn Trp Val Arg Gln Ala Pro Gly Lys Gly Leu Glu Trp Val
        35                  40                  45

Gly Trp Ile Ala Thr Ala Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Pro His Ala Ala Gly Ala Ala His Trp Tyr Phe Asp Val
            100                 105                 110

Trp Gly Gln Gly Thr Leu Val Thr Val Ser Ser
        115                 120

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30
```

```
Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg
            100                 105
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Phe Thr Phe Asp Asp Tyr Ala Met His
 1               5                  10
```

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Gly Phe Thr Phe Asp Ala Ala Ala Met His
 1               5                  10
```

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Ala Ile Thr Trp Asn Ser Gly His Ile Asp Tyr Ala Asp Ser Val Glu
 1               5                  10                  15

Gly
```

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ala Ile Thr Trp Asn Ala Gly His Ile Asp Ala Ala Asp Ala Val Glu
 1               5                  10                  15

Gly
```

```
<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Ser Tyr Leu Ser Thr Ala Ser Ser Leu Asp Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ala Ala Leu Ser Thr Ala Ser Ser Leu Asp Ala
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ser Tyr Ala Ser Thr Ala Ser Ser Leu Ala Tyr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Ser Gln Gly Ile Arg Asn Tyr Leu Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Ala Gln Gly Ile Arg Asn Ala Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Ala Ala Ser Thr Leu Gln Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ala Ala Thr Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Arg Tyr Asn Arg Ala Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Arg Ala Asn Arg Ala Pro Ala Thr
1               5

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Val Arg Gln Ala Pro Gly Lys Gly Leu Glu Trp Val Ser
1               5                   10
```

```
<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Trp Gly Gln Gly Thr Leu Val Thr Val Ser Ser
1               5                   10

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Tyr Gln Gln Lys Pro Gly Lys Ala Pro Lys Leu Leu Ile Tyr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30
```

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Phe Gly Gln Gly Thr Lys Val Glu Ile Lys
1               5                   10

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 54
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ala Gly His Ile Asp Ala Asp Ala Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 56
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ala Ala Leu Ser Thr Ala Ser Ser Leu Asp Ala Trp Gly
            100                 105                 110

Gln Gly Thr Leu Val Thr Val Ser Ser
        115                 120
```

```
<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Ala Ser Thr Ala Ser Ser Leu Ala Tyr Trp Gly
            100                 105                 110

Gln Gly Thr Leu Val Thr Val Ser Ser
        115                 120

<210> SEQ ID NO 58
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
        35                  40                  45

Ser Ala Ile Thr Trp Asn Ala Gly His Ile Asp Ala Ala Asp Ala Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 59

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ala Ala Leu Ser Thr Ala Ser Ser Leu Asp Ala Trp Gly
            100                 105                 110

Gln Gly Thr Leu Val Thr Val Ser Ser
        115                 120
```

<210> SEQ ID NO 60
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Ala Ser Thr Ala Ser Ser Leu Ala Tyr Trp Gly
            100                 105                 110

Gln Gly Thr Leu Val Thr Val Ser Ser
        115                 120
```

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
            35                  40                  45

Ser Ala Ile Thr Trp Asn Ala Gly His Ile Asp Ala Ala Asp Ala Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ala Ala Leu Ser Thr Ala Ser Ser Leu Asp Ala Trp Gly
            100                 105                 110

Gln Gly Thr Leu Val Thr Val Ser Ser
         115                 120
```

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Ala Ile Thr Trp Asn Ala Gly His Ile Asp Ala Ala Asp Ala Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Ala Ser Thr Ala Ser Ser Leu Ala Tyr Trp Gly
            100                 105                 110

Gln Gly Thr Leu Val Thr Val Ser Ser
         115                 120
```

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Ala Lys Val Ala Ala Leu Ser Thr Ala Ser Ser Leu Asp Ala Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Ala
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Ala Ser Thr Ala Ser Ser Leu Ala Tyr Trp Gly
            100                 105                 110

Gln Gly Thr Leu Val Thr Val Ser Ser
        115                 120

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

```
<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ala Gln Gly Ile Arg Asn Ala
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ala Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Ala Asn Arg Ala Pro Ala
                85                  90                  95

Thr Phe Gly Gln Gly Thr Lys Val Glu Ile Lys
            100                 105

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ala Gln Gly Ile Arg Asn Ala
            20                  25                  30

Leu Ala Trp Tyr Gln Gln Lys Pro Gly Lys Ala Pro Lys Leu Leu Ile
            35                  40                  45

Tyr Ala Ala Ala Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ala Gln Gly Ile Arg Asn Ala
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Ala Asn Arg Ala Pro Ala
                85                  90                  95

Thr Phe Gly Gln Gly Thr Lys Val Glu Ile Lys
            100                 105

```
<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Ala Asn Arg Ala Pro Ala
                85                  90                  95

Thr Phe Gly Gln Gly Thr Lys Val Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ala Gln Gly Ile Arg Asn Ala
            20                  25                  30

Leu Ala Trp Tyr Gln Gln Lys Pro Gly Lys Ala Pro Lys Leu Leu Ile
        35                  40                  45

Tyr Ala Ala Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Ala Asn Arg Ala Pro Ala
                85                  90                  95

Thr Phe Gly Gln Gly Thr Lys Val Glu Ile Lys
            100                 105
```